United States Patent [19]

Kwan-Gett

[11] 4,016,884

[45] Apr. 12, 1977

[54] ATRIOTOMY ACCESS DEVICE

[76] Inventor: Clifford S. Kwan-Gett, 2208 E. 900 South, Salt Lake City, Utah 84108

[22] Filed: July 2, 1975

[21] Appl. No.: 592,405

[52] U.S. Cl. .......................... 128/348; 128/214 R; 128/325; 128/DIG. 26

[51] Int. Cl.² ...................................... A61M 25/02

[58] Field of Search ............... 28/1 R, 214 R, 325, 28/348–351, DIG. 26

[56] References Cited

UNITED STATES PATENTS

| | | | |
|---|---|---|---|
| 1,918,890 | 7/1933 | Bacon | 128/334 C |
| 2,453,056 | 11/1948 | Zack | 128/334 C |
| 2,835,253 | 5/1958 | Borgeson | 128/303 R |
| 2,898,913 | 8/1959 | Ritter et al. | 128/325 X |
| 3,046,988 | 7/1962 | Moreau et al. | 128/349 B |
| 3,402,710 | 9/1968 | Paleschuck | 128/348 X |
| 3,783,868 | 1/1974 | Borros | 128/348 X |

OTHER PUBLICATIONS

Nose et al., Trans. ASIO –vol. x, 1964, pp. 140–146.

Primary Examiner—Dalton L. Truluck
Attorney, Agent, or Firm—Criddle, Thorpe & Western

[57] ABSTRACT

An atriotomy access adaptor for use in open-heart surgery consists of a polymeric foam base adapted to fit into an incision in the atrium. Venous uptake cannulas are inserted through incisions made in the foam adaptor base and are held in place by two loops fastened to the foam body which are adapted to allow the downward positioning of the cannulas into the atrium, but which resist withdrawal of the cannulas. Also attached to the foam base is a tab containing an elastomeric band attached to one end. When the adaptor base is inserted into the atrium the rubber band is wound around and over the atrial tissues at the point of incision insuring a snug fit of the adaptor base around the cannulas and securing the atrium around the adaptor base. The end of the elastomeric band is then anchored to the tab.

9 Claims, 4 Drawing Figures

ATRIOTOMY ACCESS DEVICE

BACKGROUND OF THE INVENTION

This invention relates to an atriotomy access device consisting of an adaptor capable of holding single or multiple venous uptake cannulas. More specifically, this invention relates to an atriotomy access device consisting of an adaptor capable of holding venous uptake cannulas in a fixed position and requiring only one incision into the atrium for insertion of one or two cannulas while maintaining a leak proof seal between the atrium and cannulas.

With the advent of open-heart surgery various techniques have been developed to allow access into various portions of the heart. In most open-heart surgeries two venous uptake cannulas are placed through two separate incisions in the right atrium of the heart for access into the superior vena cava and to the inferior vena cava for heart-lung machine support. In performing such surgery it is necessary to make double incisions which creates a greater chance of blood leakage around the incisions and tearing of the atrium. The creation of an incision in the atrium puts a limit on the time when the cannula can be inserted into the incision and also limits the manipulation of a cannula being inserted without the excess of leakage of blood.

The conventional technique of inserting a cannula into the atrium consists of making the incision, inserting the cannula and then threading or fastening a purse string suture in the atrial tissue around the atriotomy, passing said purse strings through a rubber tourniquet choker, drawing the purse strings around the atrium surrounding the atriotomy, and utilizing a clamp to fasten the purse strings in a fixed position. A fastening ligature is then tied around the rubber choker and the cannula to keep them in place.

Such an atriotomy procedure generally requires two clamps, two rubber chokers, two fastening ligatures and two purse string sutures, in addition to two incisions and two cannulas.

OBJECTS OF THE INVENTION

It is an object of this invention to provide an atriotomy adaptor device which will allow one or two cannulas to be placed through a single incision in the atrium.

It is a further object of this invention to provide an atriotomy device which prevents the leakage of blood of air from or to the atrium around or through the catheters, adaptor or incision.

A still further object of this invention is to provide an atriotomy device which minimizes the time required for surgery and results in the lessening blood loss and the chances of tearing the atrium during surgery.

A still further object of this invention is to provide an atriotomy device wherein the access cannula can be inserted or removed at any convenient time and reinserted, if desired, without requiring additional incisions or suturing.

A still further object of this invention is to provide an atriotomy adaptor device which is flexible so that manipulation of one or more cannulas is possible without causing excess leakage of blood.

These and other objects may be accomplished by means of the atriotomy adaptor device consisting essentially of a foam compressible adaptor having incisions therein for the insertion of the cannulas. The adaptor contains loops fixedly attached to the adaptor which are preferably made of a polymeric material which is flexible but not expandable. The loops are so placed to allow the downward movement of the cannulas through the loops and into the incisions in the atriotomy adaptor, but which inhibit or prevent the backward movement or removal of the cannulas without first depressing the loops toward the adaptor surface. Also attached to the adaptor surface is a tab having attached at the end thereof an elastomeric band which, when the adaptor is inserted into the incision in the atrium, may be tightly wrapped around the atrial tissue thereby sealing the atrial tissue surrounding the incision or atriotomy to the adaptor device and preventing the passage of air or blood into or out of the atrium between the atrial tissue and the adaptor device.

The novel features of this invention both as to the manner of construction or organization as well as the placement of the device into the atrium will be better understood with reference to the following descriptions and drawings. It is to be understood, however, that the description and drawings are for the purpose of illustration only and are not intended to be a definition as to the scope of this invention.

DRAWINGS OF THE INVENTION

DETAILED DESCRIPTION OF THE DRAWINGS

Figure 1:
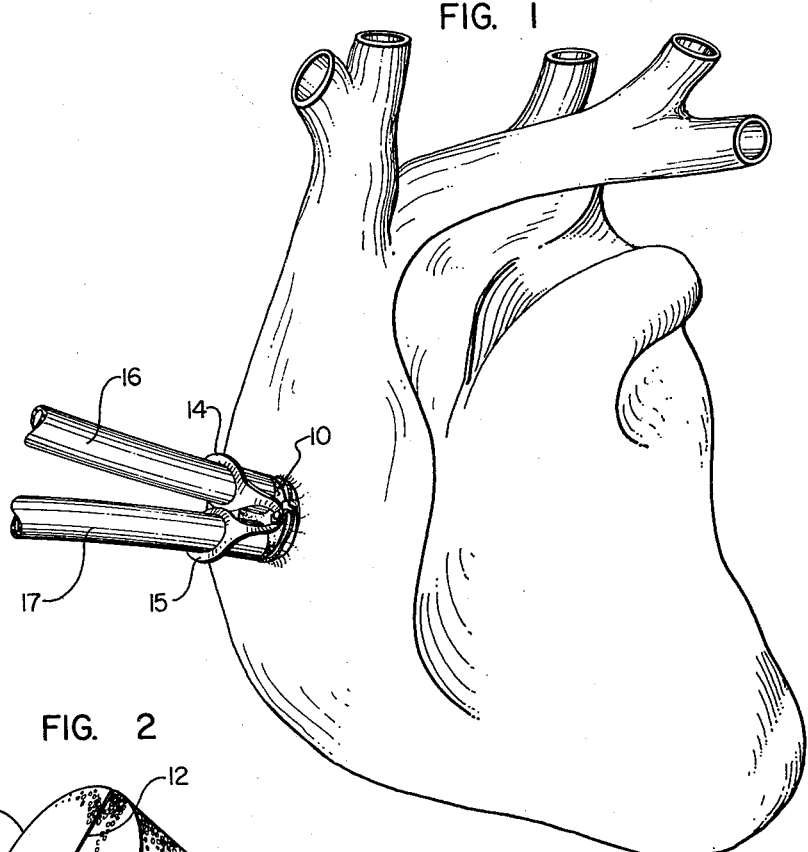
FIG. 1 is a perspective view of the atriotomy adaptor device inserted into the right atrium of the heart.

Referring now to the drawings:

There is shown in FIGS. 1 to 4 operative embodiment of the atriotomy adaptor device of the present invention. The main operational component of the apparatus is a flexible base 10 which is made of compressible foam such as a foamed polyurethane, polystyrene, polyethylene, polypropylene, silicone rubber or a foamed copolymer such as a styrene-butadiene-styrene copolymer. The specific type of material is not critical except that when compressed it must be impervious to the passage of air and liquids such as blood. If the foamed material is not of itself impervious to the flow of air and liquids it may be covered with a plastic film or coating. The adaptor must be compressible and capable of being distorted and returned to its natural shape. It is, of course, also important that this material be insoluble in blood and be inert so as not to inflame or irritate the tissues it comes in contact with when inserted into the incision in the atrium.

Figure 2:
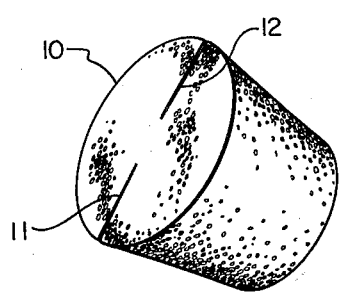
FIG. 2 is a perspective view of the atriotomy adaptor showing the incisions.
Figure 3:
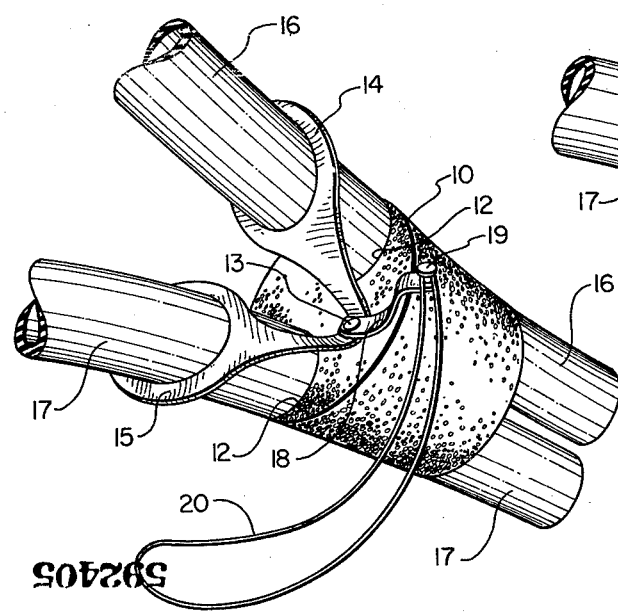
FIG. 3 is a perspective view of the atriotomy adaptor device which contains two uptake cannulas.

The adaptor 10 may be any shape, cylindrical or oval will probably be most common, however, other shapes may also be used without departing from the scope of the invention. For example, the adaptor may be the same shape as the incision of cannulas to be inserted. The adaptor 10 can also be made in different sizes and widths depending upon the subject upon which it is to be used. For example, an adult male would have a larger atrium than would a small female or a child. It is preferred, however, that the adaptor be tapered from front to back as illustrated in FIGS. 2 and 3 for ease of insertion into the atrial incision. Extending through the width of the adaptor from the front to the back and in predetermined positions are one or more incisions, illustrated in FIG. 2 as two incisions 11 and 12. The incisions will usually be a straight line extending to the periphery of the adaptor or may be in the shape of an "X", star or at right angles. Fixedly attached to the upper surface of adaptor 10 by attaching means 13 are two loops 14 and 15 which are preferably of unitary construction but may be made separately if so desired. These loops are so designed to flex upwardly and have a loop diameter substantially the same as cannulas 16 and 17. As is best illustrated in FIG. 3, cannulas 16 and 17 can be inserted through the holes in loops 14 and 15 and pushed downwardly through the openings 11 and 12 in the adaptor base. Openings 11 and 12 are maintained in a sealed relationship because of their compressibility prior to the insertion of cannulas 16 and 17 thereby inhibiting the flow of air and or blood through the adaptor. Due to the compressibility of adaptor 10, cannulas 16 and 17 may be forced through incisions 11 and 12 maintaining a fluid tight relationship between the outer surface of cannulas 16 and 17 and the inner surface of incisions 11 and 12.

Figure 4:
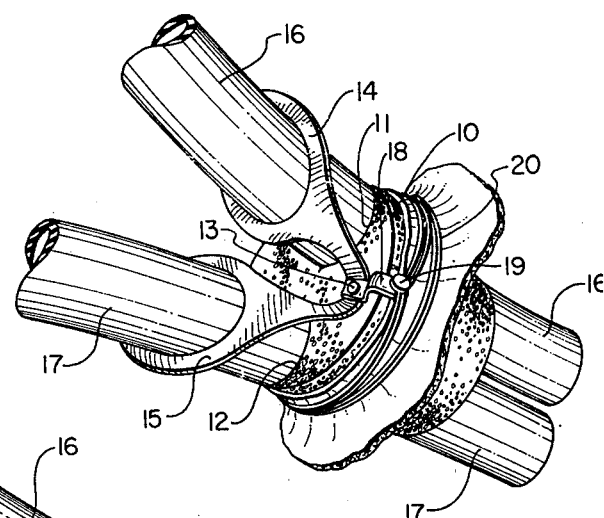
FIG. 4 is a closeup partial sectional perspective view of the atriotomy device as illustrated in FIG. 1.

Loops 14 and 15, as illustrated in FIGS. 3 and 4, extend upwardly from the base of adaptor 10 on a plane which is angular to and not necessarily parallel with the surface of adaptor 10. Since loops 14 and 15 are flexible, any downward pressure exerted by a cannulas 16 or 17 causes loops 14 and 15 to maintain a more or less parallel relationship with the surface of adaptor 10 and allows the cannulas to be slid downwardly through the loops and into the incisions 11 and 12. However, the backward movement of cannulas 16 and 17 is inhibited by the angular positioning of loops 14 and 15 so that the cannulas will not be accidentally removed during surgery. In order to remove a cannula it is necessary to depress the loop through which the cannula is extended into a parallel relationship with the surface of adaptor 10 and then pull outwardly on the cannula.

Also attached to the surface of adaptor 10 is a tab section 18 which may conveniently terminate with an upwardly extending shaft 19, having an enlarged head portion. An elastomeric band 20 is attached at one end to shaft 19 and when the atriotomy is performed and the adaptor base inserted into the incision the rubber band 20 is wound around and over the atrial tissues surrounding the incision as illustrated in FIG. 4, insuring a snug fit of the atrial tissues against the cannulas and the adaptor base. The number of times that elastomeric band 20 will be wound about is, of course, depended upon the length and elasticity of the band. However, after being wound about the atrial tissues as illustrated in FIG. 4, the band is attached to tab section 18 by being placed over shaft 19 thereby firmly anchoring the adaptor base into the incision in the atrium and further sealing the incised atrial wall tissue against the adaptor.

Obviously, the atriotomy access device according to this invention allows for several options during the surgical procedure. For example, the cannulas can be inserted before or after insertion of adaptor 10 into the atrium. If adaptor 10 is inserted into the atrium first and the atriotomy is sealed by means of elastic band 20 being wrapped around the atrial tissue, the incisions 11 and 12 in the adaptor will be compressed and will not allow the passage of blood or air to or from the atrium. In some instances it may be desirable for the surgeon to insert his finger through the performed incisions in the adaptor base and feel for the presence of any defect in the wall between the left and right atria or for regurgitation of blood through the mitral and tricuspid valves. The uptake cannulas can then be placed after the surgeons finger has been removed.

An additional advantage of the invention is that the adaptor can be placed in the atrium at any convenient time and the access cannula or cannulas can be inserted or removed as desired and samples can be taken by inserting tubes or rods without requiring any additional cutting or suturing and without danger of further tearing of the incision in the atrium. Moreover, the adaptor is flexible so that manipulation of one or both cannula tubes is possible without the leakage of blood. Even when the cannulas are removed the resiliency of the adaptor material causes the adaptor incisions to remain sealed.

Although the invention as has been described is deemed to be that which would form the preferred embodiment of the invention, it is recognized that departures may be made therefrom without departing from the scope of the invention which is not to be limited to the specific details disclosed, but to be accorded the full scope of the claims so as to include any and all equivalent devices.

What is claimed is:
1. An atriotomy access device comprising:
 a. an adaptor body consisting of a resilient, compressible polymeric foam material which is tapered inwardly from front to back and which has extending through the width thereof from front to back at least one but not more than two incisions; and
 b. a tab section attached to the adaptor body having an elastomeric band connected thereto which, when the adaptor body is inserted into the atrium, will wrap around the atrial tissue adjacent to the incision in the atrium and be anchored to said tab thereby sealing the adaptor body to the atrium incision walls in an air and fluid tight relationship.

2. An atriotomy access device as claimed in claim 1 wherein at least one but not more than two uptake cannula tubes are extended through the incisions in the adaptor body such that an air and fluid tight relationship is created between the adaptor incisions and the external surface of said cannula tubes.

3. An atriotomy access device as claimed in claim 2 wherein there is attached to the adaptor body one or more flexible upwardly extending loops in alignment with the incisions in the adaptor body through which the uptake cannyla tubes pass before being inserted through the incisions in the adaptor body, said loops being so formed that the cannula tubes may be pushed downward through the adaptor body but resist being pulled out or removed.

4. An atriotomy access device as claimed in claim 3 wherein the adaptor body has inserted there one uptake cannula tube.

5. An atriotomy access adaptor device as claimed in claim 3 wherein the adaptor body has inserted therein two uptake cannula tubes.

6. A method of anchoring an atriotomy access device into the atrium of a heart which comprises:
 a. making an incision into the right atrium of the heart,
 b. inserting therein an adaptor body consisting of a substantially resilient, compressible polymeric foam material, said adaptor body being tapered inwardly from front to back and having one or more incisions extending through the width thereof from front to back; and c. forming an air and fluid tight seal between the atrium incision and adaptor body by winding an elastomeric band attached to a tab section forming part of the adaptor body around the atrial tissues surrounding the incision and attaching said band to said tab section.

7. A method of inserting an atriotomy access device into the right atrium of a heart as claimed in claim 6 wherein the top adaptor surface has anchored thereto one or more flexible loops extending upwardly which are in alignment with the incisions in the adaptor body, and wherein one or more uptake cannula tubes are inserted through said loops and said incisions in the adaptor body and into the superior or inferior vena cava of the heart.

8. A method according to claim 7 wherein one uptake cannula tube is inserted through said flexible loop and adaptor body.

9. A method according to claim 7 wherein two uptake cannula tubes are inserted through said flexible loops and through the adaptor body.

* * * * *